United States Patent [19]

Püschel et al.

[11] Patent Number: 4,879,246

[45] Date of Patent: Nov. 7, 1989

[54] METHOD AND DEVICE FOR MINERALIZATION OF CARBONACEOUS MATERIAL

[75] Inventors: Petr Püschel; Zdenek Formánek, both of Most; Václav Krivanek, Louny-Dobromerice; Antonín Pokorny, Most; Anna Vlasáková, Most; Alena Stuchíková, Most, all of Czechoslovakia

[73] Assignee: Tessek sdruzeni Praha, Prague, Czechoslovakia

[21] Appl. No.: 116,435

[22] Filed: Nov. 3, 1987

[30] Foreign Application Priority Data

Nov. 3, 1986 [CS] Czechoslovakia ............... 7950-86
Jun. 18, 1987 [CS] Czechoslovakia ............... 4502-87

[51] Int. Cl.$^4$ .................... G01N 25/22; G01N 31/12
[52] U.S. Cl. ................................ 436/145; 436/160; 422/68; 422/78
[58] Field of Search ................ 422/78, 80, 68, 101; 436/20, 73, 77, 79-81, 146, 155, 160, 145, 177, 181

[56] References Cited

U.S. PATENT DOCUMENTS

| | | | |
|---|---|---|---|
| 3,895,906 | 7/1975 | Kottmeier | 432/105 X |
| 3,957,441 | 5/1976 | Baba | 436/77 X |
| 4,017,404 | 4/1977 | Habeger | 436/35 X |
| 4,094,640 | 6/1978 | Iwantscheff | 422/78 X |
| 4,255,386 | 3/1981 | Schachter | 436/21 X |
| 4,347,216 | 8/1982 | Kawasaki | 436/177 X |

Primary Examiner—Barry S. Richman
Assistant Examiner—Rebekah A. Griffith
Attorney, Agent, or Firm—Klein & Vibber

[57] ABSTRACT

A method and device for mineralization of carbonaceous materials, for determining trace concentration of chemical elements in foods, fodder, plant, and animal tissues and other materials. The method can also be used for determining the structure of the mineral skeleton of carbonaceous materials or for preparing ash of carbonaceous materials for various technological uses. The method includes heating a specimen to a temperature ranging from 300° to 400° C. for 6 to 20 hours at atmospheric pressure in a stream of oxygen, at a rate of 0.03 to 0.15 ml.s$^{-1}$.g$^{-1}$ of the specimen. A gas with a higher oxydative strength than that of oxygen is added to the stream of oxygen, said gas being selected from the group consisting of ozone, nitrogen oxides, chlorine and mixtures thereof such as an ozone-nitrogen oxides mixture, chloroxides of nitrogen, in an amount of 1 to 6 volume percent. The device for performing the improved method consists of a mineralization unit comprising a heatable block, provided with flatbottomed cylindrical holes for inserting the mineralization flasks containing the specimens. The block is covered by a lid, provided with openings for the necks of the flasks. Said mineralization flasks being cylindrically conically tapered towards the cylindrical neck. Inlet capillaries are loosely inserted into said openings and are at their top parts connected with the distributor of the gas mixture stream.

11 Claims, 1 Drawing Sheet

METHOD AND DEVICE FOR MINERALIZATION OF CARBONACEOUS MATERIAL

FIELD OF THE INVENTION

The invention relates to a method for the mineralization of carbonaceous material, for example by following dissolution and chemical analysis, for determination of the content of chemical elements, including trace elements in foods, fodder, in plant and animal tissues and other materials.

The decomposition of carbonaceous materials for chemical analysis presents itself as a method of treatment of a solid or liquid specimen in either genuine or pre-treated state, e.g. by grinding, drying or homogenization. The decomposition consists of two steps: The mineralization, i.e. oxidation of carbonaceous compounds present, and in the dissolution of the mineral residue, the two steps being carried out, if desired, simultaneously. The product of the decomposition is a homogeneous solution. This solution can be chemically analyzed by either chemical or physico-chemical methods. The limiting factor in determination of elements, particularly of trace elements, is their concentration in blank tests. The latter include all increments and decrements of the sought elements, occurring during the treatment of the specimen of the tested matter, until the end solution. Thus, this method includes also the manipulation with the specimen, use of tools, aids and chemical glassware, influence of the purity and amounts of the chemicals used, as well as further objective and subjective influences of the workers preparing the specimen. The background established by blank tests is then used for the correction of the results of the analysis. In analytical chemistry it is advantageous to use a method of the decomposition that uses only a small number of decomposition steps, and a small amount of chemicals. Thus, the ratio of the concentration of the sought substance in the specimen and in the blank test is favorably influenced. In this way it is possible to attain a more suitable limit of the estimation of accuracy and reproducibility of the results. The whole analytical system, i.e. the process of taking the specimen of the respective material until the results of the analysis are finally arrived at, possesses a high degree of accuracy and reliability, which is the main goal in the analytical chemistry.

DESCRIPTION OF PRIOR ARTS

The known methods of mineralization of carbonaceous materials, such as, for example, all sorts of foods, forages, animal and plant tissues use either wet or dry techniques of decomposition, or a combination thereof.

Wet decomposition of the specimen is, for example, the mineralization according to Kjeldahl, described in "Zeitschrift fuer Analytische Chemie," page 366 (1883), where the specimen is combusted in the medium of a great surplus of concentrated sulfuric acid, said acid being, in presence of a catalyst, and simultaneously an oxidation agent. Kahan's method, published in "Zeitschrift fuer Analytische Chemie", 107, page 11 (1937) uses, under similar conditions, a mixture of nitric, perchloric and sulfuric acids. The disadvantage of this method is the high acid concentration and the presence of the catalyst in the resulting solution, further requiring the additional step of separating the eventual insoluble remainder and its dissolution by another method.

Wet methods of mineralization are often modified by methods recommended by producers of analytical apparatuses, e.g. see the material of the company Varian Techtron, "Food analysis by atomic absorption" (1073). Such methods consist in the defined actions of various combinations of acids and further chemical agents on the analyzed specimen. Thereby a leach of the specimen is obtained rather than a true solution. The sought substance is only partly, and undefinably dissolved, and its remainder is bound onto the solid particles contained in the leach with various strength. This fact decreases considerably the exactness of the chemical analysis.

The decomposition in a Paar's bomb, described e.g. by Pueschel in "Zpravodaj VUHU (Report of the Research Institute of Brow Coal", Most, Page 3 (1972), and in the materials of the company Hans Kuerner, Neuberg (1984), consists in combustion of the specimen in oxygen under pressure, flushing the bomb, separating the undissolved particles, and then dissolving them in acids. The shortcoming of this method is the bad solubility of the remainder, melted together at high temperatures of the calcination, extensive manipulation with the specimen and contamination from the metallic, (though) telfonized bomb internal surface. All of these shortcomings lead to high and fluctuating concentration of the sought substance in blank tests, whereby the accuracy of the analysis is limited: For example, the burning of the specimen in the air at the temperatures ranging from 500° to 850° C., if desired in presence of sulfuric acid, as described by Feinberg and Ducauze, "Analytical Chemistry" 52, Page 207 (1980) causes losses of volatile elements such as Cd, Pb and As. Also, burning in an air stream with nitric acid vapors at 550° C., published by Gag in the "The Analyst" 80, page 789 (1955) was verified but for lead, moreover there were observed remnants of the incompletely combusted organic matrix.

Another method of mineralization of the specimens for chemical analysis is combustion in a low-pressure plasma discharge, published by Cleit, C. E., and Holland, W. D., in the "Analytical Chemistry" 34, 1454 (1962). The combustion is carried out under pressure of several hundred Pa at temperatures below 200° C. The low temperature decreases the losses of the sought substance by volatilization, but on the other hand, however, the use of a low pressure diminishes this effect considerably. A further shortcoming is the need for rather complicated and expensive apparatus, and troublesome manipulation with the specimen.

Further used methods of mineralization were published by Cibulka et al in the book "Pohyb olova, kadmia a rtuti v zemedelske vyrobe a biosfere" (The Travel of Lead, Cadmium and Mercury in agriculture production and biosphere), edited by SZN (State Agriculture Editory) in Prague (1986). It uses a sequence of operations: carbonization of the dry substance of the specimen at 400° C., long-time combustion at 500° C., subsequent mineralization by concentrated nitric acid and calcination at 500°-550° C. The use of comparatively high temperature is again disadvantageous. The use of comparatively high temperature is again disadvantageous, as well as the exacting manipulation of the specimen, so that a contamination and partial loss of the substance are possible.

In sum, the equipment for dry mineralization used up to date can be divided in three groups:

(1) The first group consists in equipment working in an open system. Such equipment makes possible drying of the mineralized material and following carbonization and final combustion in the presence of air, or, if desired, in an atmosphere with an increased oxygen content at atmospheric pressure and at a final temperature of 450° to 850° C. The combustion flasks can be made from, for example, a ceramic material, quartz or silicate glass. The combustion medium is usually formed by an electrically heated oven with regulation. For the drying and the carbonation phases one can use also electric or gas heaters, heated plates or heated blocks, partly surrounding the flasks. All this equipment has the shortcoming of being ("too open"). The result is an increased possibility of contamination, undesired particularly in trace- and ultra-trace analysis.

The comparatively high temperature can, in addition, cause a loss of some of the sought elements, or an agglomeration can at such high temperatures occur, or even melting of ashes which can be then dissolved but with great difficulty.

(2) The second group consists in equipment working at an increased oxygen pressure in a closed system. This group is represented by equipment consisting of a Paar's bomb with telfonized inner walls. The specimens are weighed into special microthene ® bags and in the bomb ignited by metallic or graphite igniting fibers. After the combustion of the specimen, the mineralized matter is quantitatively flushed out from the bomb and the solid part is separated and decomposed by acids. The solid part of the mineralized matter is usually formed by a melt which cannot be easily decomposed. Further shortcomings are the possibility of contamination by the metal of the bomb, and the high number of manipulations of the specimen. Still another disadvantage resides in high time requirements of the cycle caused mainly by the filtration of the mineralized matter.

(3) The last group includes mineralization equipment working with an oxygen stream in a plasma discharge at the pressure of several hundred kilopascals at temperatures of 150° to 200° C. The equipment, both electric and pressure parts, is quite complicated.

The above disadvantages in the individual methods of mineralization of carbonaceous materials are avoided by the present method, wherein the specimen is heated to a temperature 300°-400° C. for 6-20 hours at an atmospheric pressure in a stream of oxygen at the rate of 0.03 to 0.15 $ml.s^{-1}.g^{-1}$ of the specimen, adding a gas with a higher oxidation strength than that of the oxygen, said gas being selected from the group consisting of ozone, nitrogen oxides, chlorine and their mixtures, such as ozone/nitrogen oxides, chloroxides of nitrogen, in an amount of 1 to 6 volume percent.

The mineralization of carbonaceous materials according to the present invention takes place at temperatures of from 200° to 500° C. lower than in the dry mineralization methods used up to now, so that the possibility of volatilization of the analyzed elements is minimized. By the reaction of single components of the gaseous mixture there are formed unstable compounds such as nitrosyl-, peroxide or nitrosyl chloride with a higher oxidative effect than the sum of the effects of individual components combined. Due to the high oxidative strength of the gas mixture the specimen is perfectly combusted and the remainder does not need any subsequent oxidation. At the low temperature used and the controlled oxygen inlet, the specimen does not light up due to overheating that would cause loss of the estimated substance, sintering of the ashes and a decrease of their reactivity and solubility. The choice of the mixture of oxidative gases depends on the purpose for which the specimen is being decomposed. Thus, for example, if elements forming volatile chlorides, such as Ge, As, Sn, Sb, Pb and similar are to be determined, chlorine will not be used.

The structure of the ashes corresponds to that of the originally bound substances, the ashes are in activated physical form and are easily decomposed by a small amount of mineral acids. The resulting solution has therefore a low and exactly defined acid concentration. The number of operations leading to the solution is small, resulting in a small and constant value for the blank tests. The needed amounts of pure chemicals for the decomposition is minimal. The method is universal, many types of materials can be analyzed with only a small modification in conditions. If multiple equipment is used, it is possible to prepare a large number of specimens simultaneously.

SUMMARY OF THE INVENTION

The shortcomings mentioned above as to the various equipments for dry mineralization are avoided by the equipment for the mineralization of carbonaceous materials in dry phase by means of a gas phase according to the present invention. The substance of the invention lies in the use of a mineralization unit that is formed by a heatable block, preferably made of an aluminium alloy said block having a flat bottom is provided with cylindrical holes for inserting the mineralization flasks with the specimens. Each block is covered by a lid, preferably also made from an aluminium alloy. The lid is provided with openings for the necks of the mineralization flasks. The mineralization flasks have a cylindrical shape tapering conically towards the cylindrical neck. Inlet capillary tubes are loosely inserted therein, said capillary tubes being in their top parts annexed to the distributor of the mineralization gas mixture.

The distributor of the mineralization gas mixture can be connected through a cooler, condensate separator and mixing tube with an ammonia furnace, provided with inlets for oxygen and ammonia, and with an ozonizer with oxygen inlet, where the mixture of mineralizing gases is prepared.

If chlorine is used as a component of the mineralizing gas mixture, the distributor of the gas mixture is provided with an inlet for chlorine.

The distributor of the mineralizing gas mixture can be directly connected, however, with containers or sources of single gases as needed.

The block of the mineralization unit as well as the ammonia burning furnace and the ozonizer can be connected with a source of electric energy.

The mixing tube, the condensate separator, the cooler, the distributor of the gas mixture, chlorine inlet, mineralization furnace, inlet capillary tubes and their connecting elements are all made from a material resistant to oxidation.

The device for the mineralization of carbonaceous materials according to the invention makes it possible to act on the specimen in solid phase by a gas phase under pre-determined conditions. The solid phase of the specimen can be obtained, if desired, in the mineralization equipment of the invention by drying, degasification and evaporation of the semi-solid or liquid specimens. The reacting gas phase makes possible a controlled burning, where the oxidizing matter are components of the gas phase such as oxygen, ozone and nitrogen oxides. The advantage of the device for the mineralization of carbonaceous materials according to the invention is the controlled combustion shifting the reaction equilibrium towards obtaining mineralization products by a constant addition of fresh gas mixture while simultaneously leading off the gaseous mineralization products. Thus, a perfect mineralization product can be obtained, whereby the microstructure and texture are but slightly impaired in comparison with those of the original specimen and are very favorable for the following dissolution of the ashes. The device for the mineralization of carbonaceous materials according to the present invention makes it possible to control, according to a heating schedule, the drying, degassing and, in the last phase, the mineralization in such a way that the whole mineralization flask is evenly heated and any forming of unburnt sediments in the neck of the flask and any overheating of the mineralized material are avoided.

The losses of the determined elements are practically excluded due to the low mineralization temperature. The half-closed mineralization device decreases to a minimum the possibility of contamination of the specimen by impurities from the environment.

BRIEF DESCRIPTION OF THE DRAWINGS

The drawings show an example of the device for the mineralization of carbonaceous materials according to the invention wherein.

DETAILED DESCRIPTION

Figure 1:
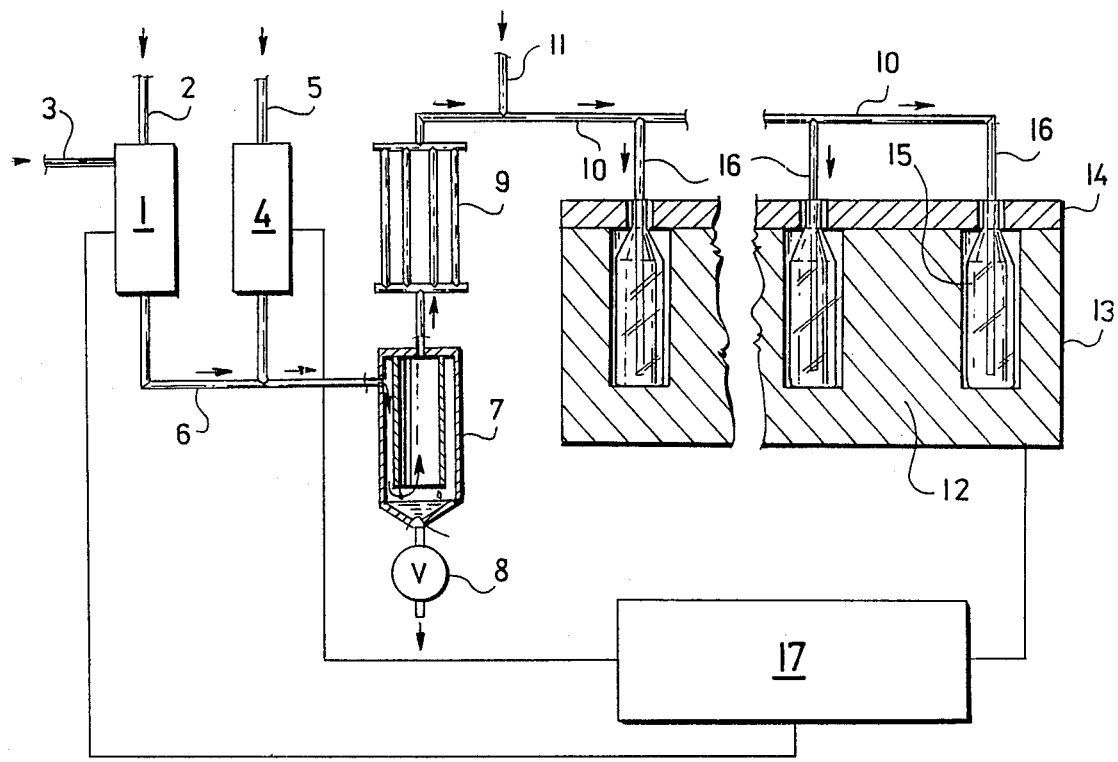
FIG. 1 is planar view of the overall apparatus for the mineralization of carbonaceous materials as disclosed in this application.
Figure 2:
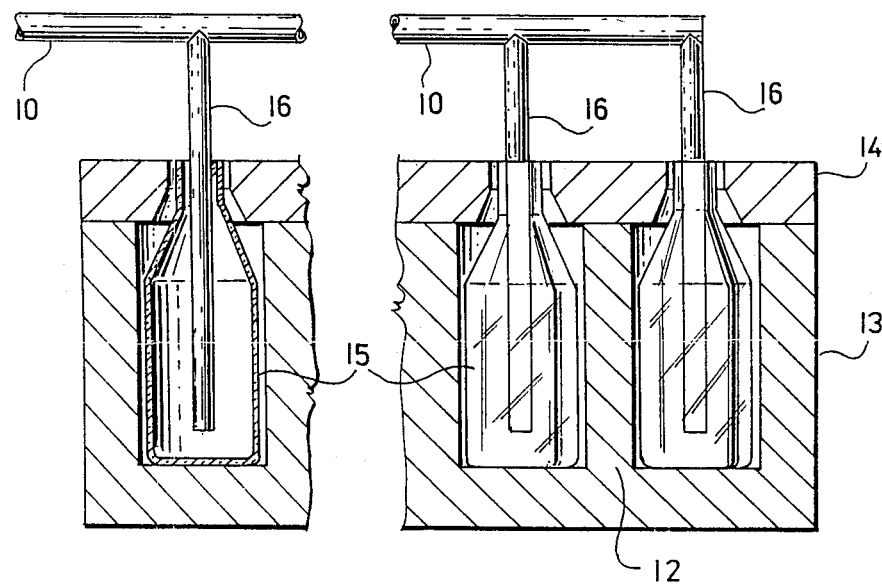
FIG. 2 is an enlarged planar view of the heatable block with the inserted mineralization flasks connected to the distributor by way of the capillary tubes.

The device for mineralization of carbonaceous materials consists of an ammonia combustion furnace 1 provided with an oxygen inlet 2 and an ammonia inlet 3, and of an ozonizer 4, provided with the oxygen inlet 5. The ammonia combusting furnace 1 and the ozonizer 4 are connected by a mixing tube 6 with a condensate separator 7, provided with an outlet 8, into which there are led the reaction products of the ammonia combusting furnace 1, i.e. a mixture of oxygen, water vapors, nitrogen oxides and reaction products from the ozonizer 4, i.e. an oxygen-ozone mixture. The condensate separator 7 is connected with the cooler 9, which is connected by the distributor 10 of the gas mixture with the mineralization unit 12. If chlorine is added to the mixture of mineralization gases, the distributor 10, of the gas mixture is provided with an inlet 11 of chlorine.

The mineralization unit 12 consists of a block 13 having, for example, a cylindrical or prismatic shape, made from an aluminium alloy, electrically heated and provided with cylindrical holes (with flat bottom) for inserting the mineralization flask 15. The specimens are inserted into said mineralization flasks. The block 13 is, on top, covered by a lid 14, also made from an aluminium alloy, provided with openings for the necks of the mineralization flasks 15. The flasks 15 are cylindrically shaped, tapering conically towards the cylindrical neck. Into the mineralization flasks 15 there are loosely inserted inlet capillary tubes 16, that are in their top part connected with the distributor 10 of the gas mixture.

To avoid undesired corrosion by the streaming mineralization gases the mixing tube 6, separator 7 of the condensate, cooler 9, distributor 10 of the gas mixture, inlet 11 for chlorine, mineralization flasks 15 and inlet capillary tubes 16 as well as their connection elements are all made from a corrosion-resistant material, such as, quartz, glass or polytetrafluoroethylene.

The device for mineralization of carbonaceous materials consists furthermore of a source 17 of electric energy, which is connected with the ammonia burning furnace 1 and the ozonizer 4 for the preparation of the mineralization gas mixture and with the block 13 for scheduled heating.

The mineralization gas mixture, for the mineralization of carbonaceous materials, is in this case prepared in the following way:

In the combustion furnace 1 is placed a mixture of ammonia and oxygen burnt on a catalyst under formation of nitrogen oxides. Another stream of oxygen is enriched by ozone in the ozonizer 4. The gases are then led together into the condensate separator 7, where the reaction water and nitric acid are separated. By the reaction of nitrogen oxides, superfluous oxygen and ozone, higher nitrogen oxides and peroxo-compounds are formed. After full separation of water from the gas mixture and, if desired, addition of chlorine to the mineralization gas mixture, the gas stream is led by the distributor 10 of the gas mixture into the inlet capillary tubes 16 to the specimens to be mineralized. The specimens are placed in mineralization flasks 15 that are in their whole volume uniformly heated, according to the program, in the mineralization block 13.

The mineralization itself is carried out so that the weighed specimens are heated according to the optimized program, regarding the character of the mineralized material. An effective action of the mineralization gas mixture is made possible by its leading into the space of the specimen, where a constant exchange of the meta-stabile, strongly oxidative reacted compounds by fresh ones takes place. The reaction products are entrained by the stream of non-reacted gas over the lid 14, of the mineralization unit 12, whereby a shift of the reaction equilibrium towards the mineralization is reached, and the stream of escaping gases thus prevents the penetration of undesired impurities into the mineralization flask 15.

ILLUSTRATIVE EMBODIMENTS OF THE INVENTION

EXAMPLE 1

A specimen of dry animal muscle, weighing 2 g, was heated for 20 hours to 400° C., in a stream of oxygen 0.06ml.s$^{-1}$, the oxygen containing 5% of nitrogen oxides.

EXAMPLE 2

A specimen of grain flour weighing 2 g was heated for 18 hours to 400° C. in a stream of oxygen containing 5% of nitrogen oxides and 1% ozone. The gas mixture was streaming at the rate of 0.2 ml.s$^{-1}$.

EXAMPLE 3

Specimen of 0.6 g of cotton was heated for 6 hours to 300° C. in a stream of oxygen 0.09 ml.s$^{-1}$, containing 5% of ozone.

EXAMPLE 4

A specimen of grain straw, weighing 1 g, was heated for 12 hours to 380° C. in a stream of oxygen containing 1% of nitrogen oxides and 5% of ozone, at a rate of 0.1 ml.s$^{-1}$.

EXAMPLE 5

Specimen of a mineral oil, weighing 2 g, was heated for 20 hours to 300° C. in a stream of oxygen containing 1% of nitrogen oxides and 5% of chlorine, at the rate of 0.1 ml.s$^{-1}$.

EXAMPLE 6

A specimen of butter, weighing 1 g, was heated for 15 hours to 350° C. in a stream of oxygen containing 5% of nitrogen oxides and 1% of chlorine, at the rate of 0.65 ml.s$^{-1}$.

In the Examples, the product of the mineralization was a loose ash easily soluble in 15% nitric acid. The ash of the grain straw and that of the flour were wetted before the dissolution with hydrofluoric and perchloric acids, whereafter the acids were boiled off.

The method of mineralization of carbonaceous materials of the present invention can be also utilized for the establishing of the structure of the mineral skeleton of carbonanceous materials or also for carefully obtaining ashes of carbonaceous materials for various technological uses.

Although the invention is described and illustrated with reference to a plurality of embodiments thereof, it is to be expressly understood that it is in no way limited to the disclosure of such preferred embodiments but is capable of numerous modifications within the scope of the appended claims.

We claim:

1. Method for the mineralization of a carbonaceous material specimen comprising the steps of
    heating the specimen to a temperature ranging from 300 to 400 degrees C. for 6 to 20 hours at atmospheric pressure in a stream of oxygen at a rate of 0.03 to 0.15 ml per second per gram of specimen,
    adding to the stream of oxygen, in an amount of 1 to 6 volume percent, a gas possessing a higher oxidation strength than that of oxygen, said gas being selected from the group consisting of ozone, nitrogen, oxides, chlorine and mixtures thereof.

2. An apparatus for the mineralization of a carbonaceous material specimen comprising
    a heatable block having a flat bottom, and mineralization flasks having necks;
    said heatable block being provided with cylindrical holes for inserting the mineralization flasks containing the specimens;
    a lid provided with openings for the necks of the mineralization flasks; said mineralization flasks having a cylindrical shape that conically tapers towards the neck;
    a plurality of capillaries loosely inserted into the necks of said flasks; and
    a distributor of a mineralization of gas mixture, said capillaries being connected to said distributor for feeding said gas mixture into said flasks.

3. An apparatus as claimed in claim 2, wherein
    the distributor of the mineralization gas is operatively connected to a cooler; and
    a condensate separator is operatively connected to said cooler;
    said condensate separator being operatively connected to a mixing tube;
    said mixing tube being operatively connected to an ammonia combustion furnace;
    said ammonia combustion furnace being provided with an oxygen inlet and an ammonia inlet; and
    an ozonizer, said ozonizer being operatively connected to said mixing tube and provided with an oxygen inlet.

4. An apparatus as claimed in claim 3, wherein
    the heatable block is connected with a source of electric energy.

5. An apparatus as claimed in claim 4, wherein
    the storing of electric energy is connected with the ammonia combustion furnaces and with the ozonizer.

6. An apparatus as claimed in claim 3, wherein the mixing tube, the condensate separator, the cooler, the distributor of the mineralization gas mixture, the mineralization flasks and the inlet capilliaries are all made from an oxidation-resistant material.

7. An apparatus for the mineralization of a carbonaceous material specimen comprising
    a cylindrical flask for mineralizing said specimen;
    said flask having a tapered neck;
    a heatable block having a cylindrical hole for inserting said flask;
    a lid for said block provided with an opening for the neck of said flask;
    a source of mineralization gas connected to a caplillary; said capillary being loosely inserted into the neck of said flask.

8. An apparatus as claimed in claim 7, wherein said source of mineralization gas comprises
    an ammonia combustion furnace and an ozonizer, said furnace and ozonizer having outlets mutually connected.

9. An apparatus as claimed in claim 8, wherein said source of mineralization gas further comprises
    a condensate separator connected to the outlets of said furnaces and ozonizer.

10. An apparatus as claimed in claim 9, wherein said source of mineralization gas further comprises
    said condensate separator having a gas outlet;
    a cooler connected to the gas outlet of said condensate separator;
    said cooler having an outlet connected to said capillary.

11. An apparatus as claimed in claim 10, wherein said source of mineralization gas further comprises
    a source of chlorine, said source of chlorine being connected to the outlet of said cooler.

* * * * *